(12) United States Patent
Boon et al.

(10) Patent No.: US 7,005,496 B2
(45) Date of Patent: Feb. 28, 2006

(54) PRODUCTION OF TRIMETHYLENE CARBONATE FROM POLY (TRIMETHYLENE CARBONATE) BY WIPED FILM REACTIVE EVAPORATION

(75) Inventors: Wyndham Henry Boon, North Canton, OH (US); David Eric Gwyn, Houston, TX (US); Thomas Clayton Forschner, Richmond, TX (US); Laurel Arden Gingrich, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/888,624

(22) Filed: Jul. 9, 2004

(65) Prior Publication Data

US 2005/0020807 A1 Jan. 27, 2005

Related U.S. Application Data

(60) Provisional application No. 60/489,797, filed on Jul. 24, 2003.

(51) Int. Cl.
*C08G 64/00* (2006.01)

(52) U.S. Cl. .................. 528/196; 422/131; 422/135; 528/198; 549/228; 549/229; 549/230

(58) Field of Classification Search ............... 422/131, 422/135; 528/196, 198; 549/228, 229, 230
See application file for complete search history.

(56) References Cited

U.S. PATENT DOCUMENTS 5,212,321 A   5/1993   Muller et al. ............... 549/228
6,054,596 A   4/2000   Ohno et al. .................. 549/228
6,580,001 B1 * 6/2003   Bowman et al. ............ 558/260

FOREIGN PATENT DOCUMENTS

DE   3418092        11/1985
DE   4109236 A1     9/1992
JP   08-134060      5/1996

OTHER PUBLICATIONS

"Studies On Polymerization And Ring Formation. III. Glycol Esters Of Carbonic Acid," by Wallace H. Carothers and F. J. Van Natta, J. Am. Chem. Soc. 52, 314 (1930) pp. 314–326.
"Study on a New Synthetic Method for Cyclic Carbonates" Hu, Bin; Zhuo, Renxi; Fan, Changlie, Huaxue Shiji (1998), 20(6), pp. 355–356 (Chinese).

* cited by examiner

Primary Examiner—Terressa Boykin
(74) Attorney, Agent, or Firm—Richard B. Taylor

(57) ABSTRACT

A method for producing trimethylene carbonate poly (trimethylene carbonate which comprises (a) introducing liquid poly(trimethylene carbonate) and an optional catalyst into a wiped film evaporator reactor under a vacuum about 15 kPa or less, said reactor having walls heated to at least about 230° C. and an internal condenser heated to a temperature above the boiling point of trimethylene carbonate, (b) spreading the poly(trimethylene carbonate) into a thin film and allowing it to flow down the interior surface of the heated walls, (c) depolymerizing the poly(trimethylene carbonate) to form trimethylene carbonate which is driven to the internal condenser and residue poly(trimethylene carbonate) which continues down the reactor, and (d) collecting the trimethylene carbonate in a cooled distillate receiver.

20 Claims, 1 Drawing Sheet

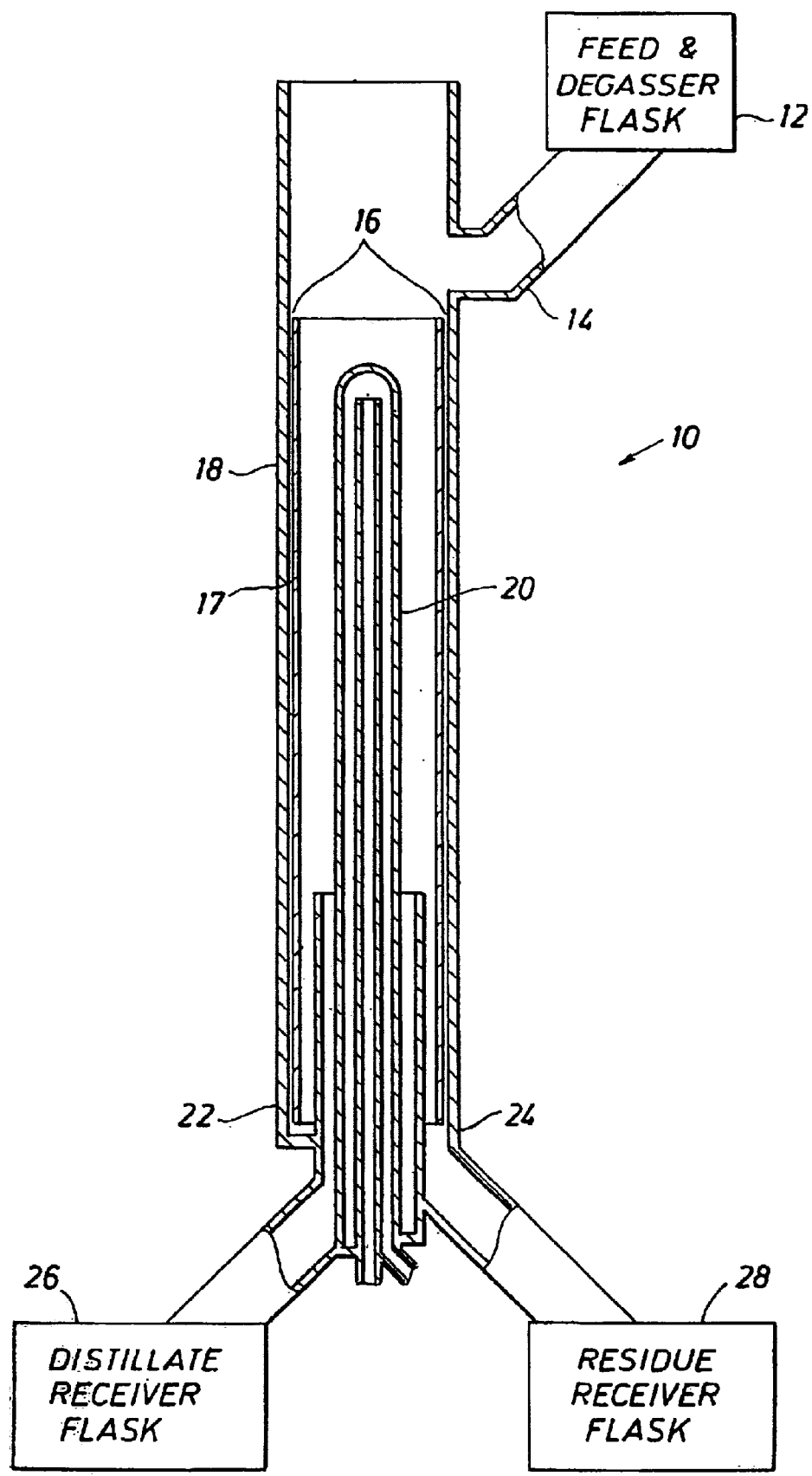

PRODUCTION OF TRIMETHYLENE CARBONATE FROM POLY (TRIMETHYLENE CARBONATE) BY WIPED FILM REACTIVE EVAPORATION

This application claims the benefit of U.S. Provisional Application No. 60/489,797 filed Jul. 24, 2003, the entire disclosure of which is hereby incorporated by reference.

FIELD OF THE INVENTION

This invention relates to a method for producing trimethylene carbonate monomer by reactive distillation of poly (trimethylene carbonate). More particularly, this invention relates to such a method involving the use of a wiped film evaporator.

BACKGROUND OF THE INVENTION

There is much information available on the production of trimethylene carbonate. Most of the prior art describes processes which go through poly(trimethylene carbonate) which is most commonly made from 1,3-propanediol and a carbonate source. The carbonate source can be dialkyl carbonates, alkylene carbonates, phosgene, urea, etc. U.S. Pat. No. 5,212,321 describes a process for producing trimethylene carbonate wherein 1,3-propanediol is reacted with diethyl carbonate in the presence of zinc powder. U.S. Pat. No. 6,054,596 describes producing cyclic carbonic esters by reacting a diol with a carbonic ester using a salt of a weak acid with an alkali metal or an alkaline earth metal as a catalyst.

All of this prior art utilizes batch reactive distillation of the poly(trimethylene carbonate) (PTMC) to trimethylene carbonate (TMC). However, reactive distillation of TMC from PTMC results in poor yields when done in a conventional batch distillation apparatus. The yields decrease with increasing batch size. The relatively high temperatures under which this batch reactive distillation takes place, i.e., from about 180 to about 230° C., and the relatively long length of time during which the PTMC and TMC are exposed to this temperature are the causes of a disadvantageous heat history for this distillation. This causes undesirable side reactions which can include dehydration of PTMC endgroups, further reactions of the dehydrated endgroups, decarboxylation of PTMC carbonate groups, and thermal degradation of the decarboxylated groups which result in poor yields of TMC, i.e., only from about 20 to about 70 percent, and most commonly for larger batches, less than 50 percent. Thus it can be seen that it would be advantageous to provide a continuous process which minimizes the heat history of the PTMC during the reaction to TMC.

SUMMARY OF THE INVENTION

This invention is a method for producing trimethylene carbonate (TMC) from poly(trimethylene carbonate) (PTMC) which comprises introducing a flowable viscous liquid PTMC which optionally contains a catalyst into a wiped film evaporator reactor under vacuum of about 15 kPa or less. The reactor has walls which are heated to at least about 230° C., preferably from about 230 to about 300° C., and an internal condenser which is heated to a temperature above the melting point of the TMC (which is about 53° C.), preferably from about 55 to about 70° C. Inside the reactor, the PTMC is spread into a uniform thin film, preferably by the action of rotating wiper blades, and is allowed to flow down the interior surface of the heated walls. At the temperature of the heated walls, the PTMC is depolymerized to form TMC which is volatilized and condenses on the internal condenser. Residual PTMC continues down the reactor and is collected in a heavies receiver. Finally, the TMC is collected in a cooled distillate (lights) receiver after it flows down and drips off of the internal condenser.

The preferred level of vacuum in the reactor is about 7.5 kPa or less and most preferably about 4 kPa or less, more preferably from about 0.01 to about 4 kPa. The most highly preferred temperature to which the reactor walls are heated is from about 270 to about 290° C. It is preferred that a catalyst selected from the group consisting of zinc powder, zinc oxide, tin powder, tin halides, organo tin compounds, hydrides, hydroxides, and salts of a weak acid with an alkali metal or alkaline earth metal be used, preferably in the amount of 0.1 to 5 weight percent based on the amount of the PTMC and most preferably, from 0.25 to 5 weight percent. The molecular weight of the PTMC used has a practical upper limit in that it cannot be too viscous or it will not flow at all. The preferred number average molecular weight range is 500 to 5000, most preferably 1000 to 3000, and most highly preferred 1500 to 2500.

BRIEF DESCRIPTION OF THE DRAWING

FIG. 1 shows a schematic of the internal condenser embodiment of the present invention.

DETAILED DESCRIPTION OF THE INVENTION

Vacuum distillation is a high value process for smooth separation. Homogeneous mixtures of liquids with different boiling points can be separated by distillation. Distillation under vacuum conditions is used for heat sensitive products when distillation at atmospheric pressure causes thermal decomposition. It is also used for high boiling products when distillation at atmospheric pressure causes difficulties with respect to energy losses and availability of construction material. The present process utilizes vacuum distillation since the reaction is heat sensitive because of several potential side reactions which are discussed above.

Wiped film evaporators, sometimes called stills, separate volatile from less volatile components with a gentle process which utilizes the thin film wiping action of feed liquid through a heated, usually cylindrical, vacuum chamber. The result is an efficient thermal separation technique with minimum product decomposition and maximum product quality. The performance is superior to flash evaporators, falling film stills, rotary evaporators, and other equipment. The wiped film evaporator reactor is best for this reaction because of the viscosity of the PTMC and the need for thin layers to be formed for quick volatilization of the TMC after it is formed and also because of the kinetics of the process.

The keys to the superiority of the wiped film evaporation reaction process in the present invention include the short residence time of the feed liquid, PTMC, a significantly lowered temperature due to high vacuum capability, and optimal efficiency in mass and heat transfer. The brief (a matter of seconds) exposure of the liquid PTMC to the heated walls can be enhanced by internal wiper designs which spread the liquid into a thin film with strict control of residence time, film thickness, and flow characteristics.

Another advantage of the wiped film evaporation process is that the reaction scales up approximately linearly. This is a result of both cracking and evaporation reactions which are a direct function of mass per unit quantity of heat. Therefore, doubling the surface area and the amount of heat required for the process will double the thoughput of the rector.

The following is a description of a simple apparatus which can be used to carry out the process of the present invention. Liquid feed PTMC and catalyst flows into the wiped film evaporator 10 from the feed tank 12 at the top of the reactor 10 through feed inlet 14, preferably by the action of a pump (not shown), preferably a positive displacement pump. The feed liquid flows into the reactor under vacuum and is immediately spread into a very thin film by the action of rotating wiper blades 17. The thin PTMC film flows down the evaporation surface 16. The combination of the heated walls 18 and the high vacuum inside the reactor 10 drive the more volatile TMC reaction product (the distillate) to the internal condenser 20. The less volatile unreacted residue PTMC components continue down the reactor 10. The resulting fractions, thus separated, exit through the distillate discharge outlet 22 and the residue discharge outlet 24 and are collected in the distillate (TMC) receiver flask 26 and the heavies residue receiver 28.

While it is desirable to minimize the length of time the TMC is at elevated temperature, it may be desirable to utilize an external condenser when this process is carried out in very large scale systems. In some situations, such as large scale systems which are designed to remove the TMC in the gas phase to the condenser as quickly as possible, it may be useful to include an external condenser which would be installed immediately downstream of the reactor 10. The PTMC distillate would flow through the external condenser which would be operated at pressures and temperatures within the same ranges as those used for the internal condenser.

The rotating wiper blades are an integral part of the wiped film evaporator reactor. They assist in spreading the PTMC into a thin film for more efficient volatilization of the TMC product. If the blades rotate too slowly, then they will not spread the PTMC in a thin film evenly—it will just run down the column. If the wiper speed is too high, oligomer is splashed into the TMC receiver, contaminating the product. For a 0.35 sq ft (0.033 sq meter) wiped film evaporator reactor, it is preferred that the wiper speed be from about 90 rpm to about 315 rpm. The wipers promote the volatilization of the TMC product by constantly renewing the PTMC surface of the film for the equilibrium.

At the temperature of the interior of the heated walls, about 230° C. or higher, preferably from about 230 to about 300° C., most preferably from about a 270 to 290° C., the crude PTMC depolymerizes to form mainly monomeric trimethylene carbonate and small amounts of 1,3-propanediol (PDO), as well as allyl alcohol, some low molecular weight PTMC, and fragments from the catalyst. The mechanism of this reaction is not well understood but it is theorized that it involves "back biting" of a hydroxylpropyl endgroup. The productive back biting includes reaction of the hydroxy propyl group with the carbonate unit to which it is attached. Also, some transesterification, polycondensation and other chemistries must occur since some material that is not depolymerized during the process (and recovered in the heavies residue receiver) is of higher molecular weight than the PTMC originally charged to the reaction vessel.

Generally, the temperature must be at least about 230° C. or the reaction takes place too slowly for practical operation of the process. Preferably, the temperature ranges from about 230 to about 300° C. At the upper limit of this range, some of the side chemistries will likely occur. The most highly preferred range is from about 270 to about 290° C. In this range, the reaction runs fast and well with good yields and without very much of the side chemistry reactions.

If the feed rate of the PTMC is too high, the reactor could be flooded and good separation will not be obtained and the TMC will have entrained oligomer impurities. Distillation is an equilibrium process of evaporation and condensation. The TMC product flows down the surface of the internal condenser and the residual PTMC flows down the evaporation surface of the heated reactor walls. If the feed rate is too high and too much TMC is formed, it will cause a non-equilibrium situation to form where no material is being condensed. As a result, material which would normally condense back onto the heated walls, such as oligomer, will be carried by the high vapor flow to the interior product condenser. Flooding may also be brought about by excessive vapor flow. This will cause liquid to be entrained in the TMC. The increased pressure from the excessive TMC vapor will also back up the PTMC liquid flowing down the heated walls. Depending on the degree of flooding, the maximum capacity of the column may be severely reduced, because the vapor phase TMC becomes saturated.

The feed rate of the PTMC is a factor which should be taken into account. If the feed rate is too low, the operation of the process will not be as efficient as it could be but this is not critical to obtain the reaction desired and some TMC product.

For a 0.35 sq ft (0.033 sq meter) wiped film evaporator reactor, it is preferred that the feed rate of the poly (trimethylene carbonate) ranges from about 0.1 to about 8 grams per minute. As discussed above, doubling the size of the reactor and the amount of heat for the reaction will double the throughput of the reactor.

When productive depolymerization occurs to form TMC, it is important that the TMC is removed from the PTMC rapidly. The high temperature, high vacuum, thin film, and agitation make volatilization of TMC occur very rapidly upon its formation. Once volatilized, the TMC condenses on the cool internal condenser. The condenser is maintained at a temperature above the melting point of the TMC (which is about 53° C.) and preferably from about 55 to about 70° C. The TMC has a low viscosity and flows down the condenser and drips off the bottom into the distillate (lights) receiver. All surfaces that the TMC comes into contact with must be maintained above its melting point until it reaches the distillate receiver. The distillate receiver can be maintained at a low temperature to avoid repolymerization before further purification. The small amount of PDO present in this material should be removed to reduce the likelihood of repolymerization. The material in the distillate receiver is a solid with some crystalline character.

With regard to the level of vacuum in the reactor, it is important to minimize the temperature required and to make sure the TMC is vaporized as quickly as possible. Generally, pressures about 15 kPa or less are required to obtain sufficient volatility of the TMC. Pressures about 7.5 kPa or less are preferred to obtain better efficiency and pressures 4 kPa or less will help to achieve the optimal efficiency of the column. At 0.01 kPa and 280° C., the conditions are considerably above the boiling point of the TMC. This encourages immediate volatility. 0.01 kPa is a practical lower limit for this process since the equipment available today generally has a practical lower operating limit of 0.01 kPa.

There are a number of catalysts which will catalyze the reaction in the wiped film evaporator reactor. Effective catalysts are disclosed in U.S. Pat. Nos. 5,212,321 and 6,054,596, the disclosures of which are herein incorporated by reference. Effective materials include zinc powder, zinc oxide, tin powder, tin halides, organo tin compounds, hydrides, hydroxides, and salts of a weak acid with an alkali metal or alkaline earth metal may also be used. The preferred catalysts for use herein are alkali metal carboxylates, acetates, and hydroxides. The most highly preferred catalyst is sodium acetate. The catalyst lowers the energy of activation of the reaction to the final product TMC and makes the reaction proceed easier and faster. However, the reaction can be carried out without a catalyst as evidenced by an experiment wherein 76 weight percent (by gas chromatography measurement)—99 weight percent (by NMR measurement) TMC was found in the distillate (TMC) receiver. However, an undesirably high amount of nonconverted material was collected in the heavies residue receiver. The use of a catalyst reduces the amount of nonconverted material. Generally, from about 0.1 to about 5 weight percent based on the amount of the PTMC of catalyst should be used and most preferably the amount of catalyst should be from about 0.01 to about 5 weight percent.

The molecular weight of the PTMC feed material should be considered. There will be a practical upper limit to the number average molecular weight—the polymer cannot be too viscous or it will not flow in the reactor. Also, we theorize that if the number average molecular weight is too high, the end group content of the polymer will be too low for sufficient reaction to TMC. If the number average molecular weight of the PTMC is too low, unacceptably high levels of oligomer will be collected in the distillate (TMC) receiver. Generally the number average molecular weight of the PTMC may range from about 500 to about 5000, preferably from about 1000 to about 3000, and most preferably from about 1500 to about 2500. A competing factor is the fact that less 1,3-propane diol (PDO) is produced in this reaction as the number average molecular weight of the feed PTMC is increased. The production of PDO is undesirable because it will react with TMC to form PTMC and because PDO is very hard to distill out of the TMC. If the reaction can be kept cold, the reaction of PDO and TMC occurs more slowly.

EXAMPLES

Oligomeric poly(trimethylene carbonate) was introduced into a Pope Scientific, Inc. 2 inch internal diameter glass wiped film still. The still was equipped with rotating wiper blades which were positioned about two inches (5 cm) below the PTMC feed inlet. The wiper blades spread the PTMC into a uniform thin film and kept it constantly agitated. The vacuum was connected at the distillate receiver and measured between a dry ice trap and the vacuum pump. The upper arm designed to connect to a vacuum trap was sealed and removed. The feed was pumped through a ¼ inch outside diameter stainless steel tube inside the original feed inlet to a point about 1 centimeter outside the vertical glass wall being wiped. The jacket connection nipples were replaced to accommodate circulation systems with no rubber parts.

High temperature oil was circulated through the jacket and the temperatures were measured at both the circulating pump and the jacket outlet. A water/glycol solution was circulated through the internal condenser and along other parts requiring temperatures above ambient temperature. The solution temperature was measured at the circulating pump.

The distillate, trimethylene carbonate, was collected in a cow udder receiver group for short runs and in a single flask outside a drain valve for longer runs. The receivers were kept cold with dry ice until they could be introduced to a dry box for sampling.

The conditions of operation are shown in the following tables. The samples were analyzed by gas chromatography or nuclear magnetic resonance as shown in the table. More explanation about the tables follows.

Table I gives the conditions used in the wiped film evaporator depolymerization, the number average molecular weight of the crude PTMC used as feed for the depolymerization, catalyst type, and concentration and weight of material collected in the distillate (TMC) and heavies receivers. Table IA shows results from a designed experiment. The experiment was designed to look at how particular variables impact TMC production or percent conversion. The particular variables included in the experimental model were flow rate, temperature, wiper speed, vacuum, and catalyst weight. Table II lists the gas chromatograph measurement results based on the gas chromatography analysis and the yields are based only on the crude PTMC that was reacted. The reason for this calculation is that material that reaches the heavies receiver is mainly crude PTMC that can be recycled back into the wiped film evaporator reactor. A commercial process will likely minimize the amount of heavies but will not eliminate them. Table III lists the results of the NMR analysis of only the crude PTMC that reacted and is calculated on a mole percent basis. It is important to note that the amount of oligomer is higher in the NMR analysis than in the gas chromatography analysis. This is likely the result of depolymerization of oligomer in the gas chromatography injection port. Table IV lists the results of NMR analysis of the material collected in the heavies receiver. It should be noted that the PTMC in the heavies receiver has a higher number average molecular weight than the starting crude PTMC.

It can be seen in all instances that a high percentage of trimethylene carbonate was recovered in the distillate. Thus, the yields by gas chromatography analysis were always above 90 percent by weight when calculated based on the amount of crude PTMC that reacted. The yields by NMR analysis of TMC and PTMC oligomer totaled 95+ mole percent in all systems tested. The oligomer content varied from 11 to 18 molar percent and likely would be isolated during subsequent purification of the TMC so that the oligomer could be recycled. It is desirable to minimize the oligomer produced but the most important aspect is to minimize the PDO which is produced because it will react with the TMC to make PTMC. It is acceptable to have oligomer in TMC when it is used to make oligomers.

Since the molecular weight (viscosity) of the PTMC can effect the efficiency of the reaction, the viscosities of various PTMC polymers have been measures at various temperatures. The results are shown in Table V.

TABLE I

Crude PTMC Depolymerization via WFE Distillation
Material Characterization, Process Conditions and Yields

| Sample | Temp, ° C. | Pressure, kPa | Feed MW | Feed Rate. grams/min | Catalyst | Catalyst Conc % wt | Time (a), min. | Weight (b), g Distillate (c) | Heavies (d) |
|---|---|---|---|---|---|---|---|---|---|
| 53  | 261 | 0.02 | 2366 (g) | 0.6 to 1.9 | Sn(II) Octoate | 0.5 | 33    | 40.71  | 0.26  |
| 69  | 280 | 0.03 | 2366 (g) | 8.0        | none           | —   | 14    | 85.80  | 25.64 |
| 93  | 281 | 0.11 | 2366 (g) | 8.0        | Sn(II) Octoate | 0.5 | 14.5  | 83.57  | 29.43 |
| 173 | 260 | 0.14 | 1157 (e) | 8.0        | NaOAc          | 1.1 | 17.75 | 85.70  | 57.97 |
| 187 | 280 | 0.25 | 2020 (e) | 8.0        | NaOAc          | 1.1 | 14.25 | 108.37 | 7.97  |
| 195 | 280 | 0.25 | 2020 (e) | 8.0        | NaOAc          | 1.1 | 4.83  | 38.91  | 0.09  |

(a) Time when crude PTMC was being fed into the WFE.
(b) Total weight of material collected during entire experiment. Time of collection longer than time of feeding crude PTMC; Wipers were run until all material drained from the WFE.
(c) Weight of material collected from the condenser (distillate).
(d) Weight of material collected that did not volatilize (heavies).
(e) Material made by PPG via transesterification of PDO and dimethyl carbonate.
(f) Wipers were run at 150 rpm.
(g) Material made via ring opening oligomerization of TMC using PDO as the initiator

TABLE IA

2" WFE Designed experiment

| Order as run | RUN No. (1) | ID, LR 25698 | FLOW_RATE, grams/min Target | Average | TEMPERATURE ° C. | WIPER_SPEED rpm | VACUUM kPa Target | Average | Feed grams | CATALYST wt % | TMC, % | PTMC, % | % CONVERTED |
|---|---|---|---|---|---|---|---|---|---|---|---|---|---|
| 1  | 9   | 26-2  | 5 | 5.6 | 270 | 195 | 1.73 | 1.73 | 550  | 0.63 | 85.5   | 12.9   | 89 |
| 2  | 18  | 33-2  | 8 | 8.5 | 280 | 92  | 0.13 |      | 1054 | 1    | 55.8   | 44.2   | 35 |
| 3  | 7   | 38-2  | 2 | 1.6 | 260 | 92  | 0.13 | 0.13 | 200  | 1    | 91.8   | 8.1    | 78 |
| 4  | 4   | 38-4  | 2 | 1.6 | 260 | 315 | 3.33 | 3.33 | 335  | 1    | 89.2   | 8.6    | 62 |
| 5  | 13  | 38-6  | 2 | 1   | 280 | 92  | 25   | 3.33 | 410  | 1    | 83.9   | 14.0   | 65 |
| 6  | 17  | 38-8  | 2 | 1.1 | 280 | 315 | 0.13 | 0.13 | 530  | 1    | 88.4   | 11.4   | 70 |
| 7  | 14  | 41-2  | 8 | 7.5 | 280 | 315 | 3.33 | 3.33 | 1630 | 1    | 90.5   | 8.3    | 98 |
| 8  | 8   | 41-4  | 8 | 7.5 | 260 | 315 | 0.13 | 0.19 | 2310 | 1    | 86.4   | 13.2   | 100 |
| 10 | 6   | 50-2  | 2 | 1.6 | 260 | 315 | 0.13 | 0.13 | 160  | 0.25 | 92.9   | 7.0    | 82 |
| 11 | 15  | 50-4  | 2 | 1.5 | 280 | 92  | 0.13 | 0.15 | 320  | 0.25 | 94.7   | 5.3    | 66 |
| 12 | 11  | 50-6  | 2 | 2.7 | 280 | 315 | 3.33 | 3.33 | 390  | 0.25 | 91.0   | 7.3    | 76 |
| 13 | 2   | 50-8  | 2 | 2   | 260 | 92  | 3.33 | 3.33 | 480  | 0.25 | 88.3   | 9.5    | 67 |
| 14 | 16  | 50-10 | 8 | 7.2 | 280 | 315 | 0.13 | 0.25 | 755  | 0.25 | 91.1   | 8.7    | 97 |
| 15 | 12  | 50-12 | 8 | 7.8 | 280 | 92  | 3.33 | 3.33 | 1100 | 0.25 | 70.3   | 28.2   | 34 (3) |
| 16 | 5   | 50-14 | 8 | 7.9 | 260 | 92  | 0.13 | 0.22 | 1450 | 0.25 | NR (2) | NR (2) | 22 (3) |
| 17 | 1   | 55-2  | 8 | 7.5 | 260 | 315 | 3.33 | 3.33 | 240  | 0.25 | 88.6   | 10.4   | 96 |
| 18 | 5R  | 55-4  | 8 | 7.4 | 260 | 92  | 0.13 | .23  | 690  | 0.25 | 85.9   | 13.7   | 64 (3) |
| 19 | 10.1| 58-2  | 5 | 4.9 | 270 | 195 | 1.73 | 1.73 | 480  | 0.63 | 88.8   | 9.3    | 73 |
| 20 | 10.2| 58-4  | 5 | 4.5 | 270 | 195 | 1.73 | 1.73 | 620  | 0.63 | 90.0   | 8.3    | 73 |
| 21 | 10.3| 58-6  | 5 | 4.7 | 270 | 195 | 1.73 | 1.73 | 840  | 0.63 | 88.0   | 9.8    | 72 |

(1) Run no. from model designed experiment.
(2) NR = Not run; could not get a clean product sample, oligomer contaminating product.
(3) Oligomer overflow into product, may have contaminated product.

TABLE II

Weight Percent Based on Crude PTMC Reacted - GC Analysis

| Sample | Allyl alcohol | PDO | Octanoic Acid | TMC | Unknown <C7 | BisPDO Carbonate | PTMC (C7+) | Total |
|---|---|---|---|---|---|---|---|---|
| 53  | 0.00 | 2.26 | 0.22 | 95.72 | 0.03 | 0.03 | 1.76 | 100.00 |
| 69  | 0.01 | 2.31 | 0.00 | 96.98 | 0.00 | 0.05 | 0.65 | 100.00 |
| 93  | 0.00 | 3.14 | 0.41 | 94.08 | 0.09 | 0.00 | 2.28 | 100.00 |
| 173 | 0.48 | 0.87 | 0.00 | 92.90 | 1.54 | 0.00 | 4.21 | 100.00 |
| 187 | 0.75 | 3.28 | 0.00 | 93.72 | 0.67 | 0.04 | 1.54 | 100.00 |
| 195 | 0.63 | 1.96 | 0.00 | 94.58 | 1.27 | 0.01 | 1.56 | 100.00 |

| Sample | Allyl alcohol | PDO | TMC | PTMC (C7+) | PTMC MW |
|---|---|---|---|---|---|
| 93  | 0.0 | 3.7 | 85.3 | 11.0 | 677 |
| 173 | 0.0 | 0.5 | 85.6 | 13.9 | 349 |
| 187 | 0.0 | 2.2 | 79.7 | 18.1 | 383 |
| 195 | 0.0 | 1.1 | 80.6 | 18.3 | 526 |

TABLE IV

Mole Percent of Material In Heavies Receiver - NMR Analysis

| Sample | Allyl alc. | PDO | TMC | PTMC (C7+) | PTMC MW |
|---|---|---|---|---|---|
| 69 | 0.0 | 0.50 | 11.40 | 88.1 | 2917 |
| 173 | 0.0 | 0.0 | 0.50 | 99.5 | 5557 |
| 187 | 0.0 | 0.30 | 0.00 | 99.7 | 3016 |

Viscosity Estimated 1600 MW

| | |
|---|---|
| at 65 C | 18,399 |
| at 70 C | 16,471 |
| at 75 C | 14,543 |
| at 80 C | 12,614 |
| at 85 C | 10,686 |
| at 90 C | 8,757 |
| at 95 C | 6,829 |
| at 100 C | 4,907 |

The above assumes linearity.

TABLE V

PTMC Viscosity

| Sample ID 8404- | MW | Temp °C. | Visc. @ 0.145 sec$^{-1}$ (0.5 rpm) cps | Visc. @ 0.725 sec$^{-1}$ (2.5 rpm) cps | Visc. @ 1.45 sec$^{-1}$ (5.0 rpm) cps | Visc. @ 30 sec$^{-1}$ (100 rpm) cps |
|---|---|---|---|---|---|---|
| 233 | 1118 | 50 | 9290 | 8610 | 8490 | 8170 |
| 233 | 1118 | 65 | 3020 | 3260 | 3230 | 3100 |
| 233 | 1118 | 100 | 922 | 993 | 831 | 639 |
| 233 | 1118 | 137 | 434 | 452 | 403 | 196 |
| 248 | 2020 | 50 | 82,800 | 82,600 | 81,600 | 79,600 |
| 248 | 2020 | 65 | 31,800 | 31,200 | 30,500 | 28,500 |
| 248 | 2020 | 100 | 8380 | 6300 | 5760 | 4590 |
| 248 | 2020 | 137 | 2680 | 2020 | 1790 | 1160 |
| 250-4 | 3500 | 50 | 308,000 | 308,000 | 306,000 | 298,000 |
| 250-4 | 3500 | 65 | 95,100 | 95,000 | 94,000 | 92,200 |
| 250-4 | 3500 | 100 | 12,000 | 12,000 | 11,900 | 11,600 |
| 250-4 | 3500 | 137 | 4300 | 5060 | 4740 | 3280 |

We claim:

1. A process for producing trimethylene carbonate from poly(trimethylene carbonate) which comprises:
   (a) introducing liquid poly(trimethylene carbonate) and an optional catalyst into a wiped film evaporator reactor under a vacuum of about 112 kPa or less, preferably about 15 kPa or less, said reactor having walls heated to at least about 230° C. and an internal condenser heated to a temperature above the boiling point of trimethylene carbonate,
   (b) spreading the poly(trimethylene carbonate) into a thin film and allowing it to flow down the interior surface of the heated walls,
   (c) depolymerizing the poly(trimethylene carbonate) to form trimethylene carbonate which is volatilized and condenses on the internal condenser and residual poly(trimethylene carbonate) which continues down the reactor, and
   (d) collecting the trimethylene carbonate in a cooled distillate receiver.

2. The process of claim 1 wherein the internal condenser is heated to about 55° C. to about 70° C.

3. The process of claim 1 wherein the catalyst is selected from the group consisting of zinc powder, zinc oxide, tin powder, tin halides, organo tin compounds, hydrides, hydroxides, and salts of weak acids with an alkali metal or alkaline earth metal.

4. The process of claim 3 wherein the catalyst is selected from the group consisting of alkali metal carboxylates, acetates, and hydroxides.

5. The process of claim 4 wherein the catalyst is sodium acetate.

6. The process of claim 3 wherein the catalyst is present in the amount of about 0.1 to about 0.5 percent by weight based on the amount of poly(trimethylene carbonate).

7. The process of claim 6 wherein the catalyst is present in the amount of about 0.25 to about 5 weight percent based on the amount of poly(trimethylene carbonate).

8. The process of claim 1 wherein the wiper speed is greater than the maximum speed at which the wipers will not spread the poly(trimethylene carbonate) into a thin film in the reactor and is less than the minimum speed at which any catalyst present is thrown out of the poly(trimethylene carbonate).

9. The process of claim 8 wherein the wiped film evaporator reactor has 0.35 sq ft (0.033 sq meter) available surface area and the wiper speed ranges from about 90 rpm to about 315 rpm.

10. The process of claim 1 wherein the feed rate of the poly(trimethylene carbonate) into the reactor is less than the minimum feed rate which will cause the reactor to flood.

11. The process of claim 10 wherein the wiped film evaporator reactor has 0.35 sq ft (0.033 sq meter) available surface area and the feed rate of the poly(trimethylene carbonate) ranges from about 0.1 to about 8 grams per minute.

12. The process of claim 1 wherein the number average molecular weight of the poly(trimethylene carbonate) is less than the minimum number average molecular weight at which the poly(trimethylene carbonate) is too viscous to flow down the reactor.

13. The process of claim 12 wherein the number average molecular weight of the poly(trimethylene carbonate) ranges from about 500 to about 5000.

14. The process of claim 13 wherein the number average molecular weight of the poly(trimethylene carbonate) ranges from about 1000 to about 3000.

15. The process of claim 14 wherein the number average molecular weight of the poly(trimethylene carbonate) ranges from about 1500 to about 2500.

16. The process of claim 1 wherein the reactor walls are heated to about 230 to about 300° C.

17. The process of claim 16 wherein the reactor walls are heated to about 270 to about 290° C.

18. The process of claim 1 wherein the vacuum in the reactor is about 7.5 kPa or less.

19. The process of claim 18 wherein the vacuum in the reactor is about 4 kPa or less.

20. The process of claim 19 wherein the vacuum in the reactor is from about 0.01 to about 4 kPa.

* * * * *